(12) United States Patent
Callen

(10) Patent No.: US 7,014,231 B1
(45) Date of Patent: Mar. 21, 2006

(54) POOL MAINTENANCE DEVICE

(76) Inventor: Chris D. Callen, 900-G Club Dr., Westerville, OH (US) 43081

( * ) Notice: Subject to any disclaimer, the term of this patent is extended or adjusted under 35 U.S.C. 154(b) by 0 days.

(21) Appl. No.: 11/032,861

(22) Filed: Jan. 11, 2005

(51) Int. Cl.
 *B25J 1/04* (2006.01)
 *G01F 19/00* (2006.01)

(52) U.S. Cl. .............................. 294/24; 294/26; 294/55; 73/427

(58) Field of Classification Search ................ 294/2, 294/10, 24, 26, 55; 73/426, 427; 7/164, 7/167, 170
See application file for complete search history.

(56) References Cited

U.S. PATENT DOCUMENTS

| | | | |
|---|---|---|---|
| 449,147 A * | 3/1891 | Welch | 73/427 |
| 1,836,014 A * | 12/1931 | Chamberlain | 30/327 |
| 2,189,238 A | 6/1940 | Benjamin | |
| 2,624,201 A | 1/1953 | Thomson | |
| 2,889,797 A | 6/1959 | Fox | |
| 3,692,490 A | 9/1972 | Hall | |
| 3,960,021 A | 6/1976 | Jones | |
| 4,037,554 A | 7/1977 | Foscolo | |
| 4,061,038 A | 12/1977 | Clarke, Jr. | |
| 4,083,253 A | 4/1978 | Nienow | |
| 4,454,775 A | 6/1984 | Ellis | |
| 4,515,023 A * | 5/1985 | Kershner | 73/864.51 |
| 4,869,118 A | 9/1989 | Keller | |
| 4,982,615 A | 1/1991 | Sultan et al. | |
| 5,202,094 A | 4/1993 | Jones | |
| 5,442,970 A | 8/1995 | Hutchins | |
| 5,726,363 A | 3/1998 | Kalidindi | |
| 5,974,900 A | 11/1999 | Kalidindi | |
| 6,422,623 B1 * | 7/2002 | Thomas | 294/24 |

* cited by examiner

*Primary Examiner*—Dean J. Kramer
(74) *Attorney, Agent, or Firm*—Lawson Law Offices LLC; Michele Lawson, Esq.

(57) ABSTRACT

A pool maintenance device that can be used for several tasks including: sampling water at a predetermined depth below the water surface, removing a skimmer cover, moving objects within the pool, adding chemicals to the pool, and storing pool chemicals. The device is comprised of an elongated rigid rod having opposing first and second ends with an attached sampling container and hook assembly. The container is open at the top and has a discharge facilitation area. A handle extends laterally from the opposing side of the container. The hook assembly is comprised of a base, a curved hook, and a spherical element. The hook extends laterally from the base of the hook assembly and the spherical element extends upwardly from the base so as to be positioned essentially perpendicular to the hook.

20 Claims, 3 Drawing Sheets

POOL MAINTENANCE DEVICE

BACKGROUND OF THE INVENTION

1. Field of the Invention

The present invention relates to a pool maintenance device for use in connection with general pool maintenance tasks. The pool maintenance device has particular utility in connection with taking a fluid sample from the swimming pool, removing a skimmer cover for cleaning, moving a dividing rope line, or checking a pool thermometer all without having to get on the ground thus eliminating any strain on the body.

2. Description of the Prior Art

Swimming pool maintenance normally requires purchasing a variety of separate tools. A fluid sampling apparatus is needed for collecting a fluid sample from a predetermined depth in a swimming pool in order to check the chemical balance of the water in the pool. In testing the water of swimming pools, the sample of water should be taken from at least 18" below the water's surface to ensure accuracy of results. Normally, in order to obtain this sample, a person would have to kneel on the ground or bend down beside the pool and dip a container 18" down into the water. This is very hard on the knees as well as the back, not to mention the fact that the person's arm gets wet when taking the sample.

Chemicals must be added to the pool to create the proper chemical balance. Adding chemicals to the pool entails having a second tool for pool maintenance. A measuring cup must be used to measure the correct amount of chemicals to add to the pool. These chemicals are normally stored separately from the rest of the tools needed for pool maintenance.

A third tool is needed to remove skimmer covers and clean the baskets. This exercise also involves kneeling and bending and thus exerts considerable strain on the body.

A fourth tool is needed to move a diving rope line. In order to check the pool thermometer, one has to kneel or bend down to the ground beside the pool, which is hard on the body, and put his/her arm in the water yet again to retrieve the thermometer. The present invention combines all of the above tools needed for pool maintenance into one tool that can be hung on a wall or fence and store pool chemicals.

The use of fluid samplers is known in the prior art. For example, U.S. Pat. No. 4,869,118 to Keller discloses a water retriever. However, the Keller '118 patent does not have a spherical element for use in removing skimmer covers, and has further drawbacks of not having a hook for moving a dividing rope line or picking up a pool thermometer. This invention teaches a water retriever for use in collecting fluid samples from a swimming pool. It consists of a tube with a water container supported by its lower end. A rod extends through the tube to the lid of the water container in order to lift the lid to allow water into the container. This invention does not eliminate the use of other tools for pool maintenance. The water container of this invention cannot be used for the storage of pool chemicals nor can it be used to mix and add chemicals to the pool. In addition, if the cover is affixed to the container and cannot be removed for some reason, no water can enter the container to be analyzed.

U.S. Pat. No. 3,960,021 to Jones discloses a sampling apparatus that can be used to take a fluid sample from a body of liquid. However, the Jones '021 patent does not have a spherical element to remove skimmer covers, and additionally does not have a fixed container with a handle for taking fluid samples. This invention consists of an elongated rod-like structure with a handle at one end and a collar to hold a fluid container at the other end. A decapping means is also present at the handle end of the invention. The fluid container is removable and is fitted with a cap which can be removed through use of the decapping means at the top of the invention. This invention cannot be used as an all-in-one tool for pool maintenance. Pool chemicals cannot be stored in the fluid container. There is no attachment that allows for the removal of skimmer covers and skimmer baskets for cleaning.

Similarly, U.S. Pat. No. 2,624,201 to Thompson discloses a milk sampling device that is used to take a milk sample from a container of milk. However, the Thompson '201 patent does not have a spherical element for the removal of skimmer covers, and cannot store pool chemicals in its sampling container. This invention teaches an elongated rod with a hook on one end and a series of clamping fingers on the other end. These clamping fingers are used to hold test tubes to be used as the sampling containers. This invention does not have a large enough sampling container that can be used to store pool chemicals. In addition, pool chemicals cannot be mixed in the test tube to be added to the pool. There is no attachment that will allow skimmer covers to be removed and skimmer baskets to be cleaned without bending or kneeling on the ground.

U.S. Pat. No. 5,442,970 to Hutchins discloses a water sampling device that can be used to obtain a water sample from a polluted body of water. However, the Hutchins '970 patent does not have a spherical element to remove skimmer covers, and has the additional deficiency of not having a hook to move the diving line in a pool or retrieve a pool thermometer.

This invention teaches a water sampling device consisting of a telescopically extendable pole with a handle on one end and a retaining member on the other end to which a sampling container can be attached to. A special sample container is needed as it must have a support member extending laterally from a side of the container so that it can attach to the pole member. This invention does not allow for the water sample to be taken from any depth since the device does not extend vertically into the water but instead extends horizontally into the water to reach farther out into the water. This invention cannot be used as an all-in-one pool tool since there is no way to lift skimmer covers or move the dividing rope line. Additionally, the handle does not provide any means for storage by hanging on a wall or fence.

Lastly, U.S. Pat. No. 4,061,038 to Clarke, Jr. discloses a mosquito larvae dipper that can be used to remove mosquito larvae from bodies of water. However, the Clarke, Jr. '038 patent does not have a spherical element for removal of skimmer covers, and has the additional deficiency of not having a hook for moving the dividing line in a pool or retrieving a pool thermometer from the pool water. This invention teaches a pouring dipper with graduations in metric and English units to provide an easy indication of the amount of liquid in the dipper. A removable handle is attached to a side of the dipper. This invention cannot be used as an all-in-one pool maintenance device since it does not contain a hook or a spherical element attachment that can be used for moving or removing objects.

While the above-described devices fulfill their respective, particular objectives and requirements, the aforementioned patents do not describe a pool maintenance device that allows for pool maintenance to be done with one tool. The present invention does allow for pool maintenance to be done with one tool. Unlike the Keller '118 patent, the Hutchins '970 patent, and the Clarke, Jr. '038 patent, the present invention is formed with a hook assembly on one end to allow for storage of the device on a wall or fence. The hook also can be used to move the dividing rope line in a pool. An additional benefit of the hook is utilizing it to grasp the string of the pool thermometer to pull the thermometer out of the pool to check the temperature. The hook assembly of the present invention also possesses a spherical element that can be inserted into the skimmer covers of a pool to remove them. The hook assembly can also be used to remove the skimmer baskets for cleaning. None of the above inventions possess a hook assembly feature that can be used for the above purpose. In addition, the present device has a large sampling container attached to an elongated rod structure that can be used to collect water samples for testing from the pool. This sampling container is large enough to hold 4 cups of chemicals that could be added to the pool to obtain a chemical balance. When not in use, the pool chemicals can be stored within the sampling container. Unlike the Keller '118 patent, the Jones '021 patent, the Thompson '201 patent, the Hutchins '970 patent, and the Clarke, Jr. '038 patent, the sampling container of this invention is permanently affixed to the rod structure so that the container will never be misplaced. The container also possesses a discharge facilitation area and its own handle to assist in the addition of pool chemicals to the swimming pool. Unlike some of the prior art, this pool maintenance device is lightweight and economical. One would no longer have to purchase several different tools to maintain a swimming pool. One would no longer have to worry about having room to store all of the pool tools that he or she owns. The present invention can be hung on the fence or wall by the pool. When one has many pool tools to keep track of, a pool tool could be lost or misplaced and precious time could be wasted looking for the tool. With the present invention being one tool, one could know where it was at all times. The present invention also allows for pool maintenance to be done without any strain on the body since there is no bending or kneeling on the hard ground by the pool to perform pool maintenance. This is especially beneficial for the elderly and those with knee, hip, or back problems. With the use of the present invention, one would no longer have to get wet in order to maintain a pool. The present invention would greatly ease the rigors of swimming pool maintenance.

Therefore, a need exists for a new and improved pool maintenance device that can perform pool maintenance using only one tool which eliminates any strain placed on the body. In this regard, the present invention substantially fulfills this need. In this respect, the pool maintenance device according to the present invention substantially departs from the conventional concepts and designs of the prior art, and in doing so provides an apparatus primarily developed for the purpose of using only one tool for all pool maintenance without placing any strain on the body.

SUMMARY OF THE INVENTION

In view of the foregoing disadvantages inherent in the known types of fluid collection devices now present in the prior art, the present invention provides an improved pool maintenance device, and overcomes the above-mentioned disadvantages and drawbacks of the prior art. As such, the general purpose of the present invention, which will be described subsequently in greater detail, is to provide a new and improved all-in-one pool maintenance device for maintaining a swimming pool that eliminates any strain on the body which has all the advantages of the prior art mentioned heretofore and many novel features that result in a pool maintenance device which is not anticipated, rendered obvious, suggested, or even implied by the prior art, either alone or in any combination thereof.

To attain this, the present invention essentially comprises a rigid elongated rod having opposing ends with a hook assembly fixedly attached to one end and a sampling container fixedly attached to the other end. The hook assembly is comprised of a base having opposing ends, a hook, and a spherical element. The downwardly curving hook extends laterally from one side of the base while the spherical element projects upwardly from the first end portion of the base to be positioned essentially perpendicular to the hook. The second end portion of the base of the hook assembly contains a female receptacle. This female receptacle is positioned opposite the spherical element. The first end of the rod acts as a male connector and inserts into this female receptacle so that both male and female parts lie integral to one another. The sampling container has an open top and a downwardly curving handle extending laterally from near the top on one side of the container. The handle is essentially comprised of two horizontally extending members with each horizontally extending member connecting to an opposing end of a vertically extending member. The vertically extending member of the handle contains a female receptacle into which the second end portion of the rod is inserted to attach the container to the rod. A discharge facilitation area is positioned diametrically opposed to the handle of the container. The sampling container has raised graduations with metric units on one side and raised graduations with English units on the other side. There has thus been outlined, rather broadly, the more important features of the invention in order that the detailed description thereof that follows may be better understood and in order that the present contribution to the art may be better appreciated.

The invention may also include a telescopically extending rod as opposed to a rod of fixed length. The invention can be made of any predetermined length as long as the length allows the device to extend at least 18" into the water. The pool maintenance device can be manufactured as one continuous piece or as separate pieces with opposing male/female parts that could interconnect to form the device. The invention can be made of a number of different materials such as a hard plastic, an aluminum gauge metal, stainless steel, or any material of the like. The rod can be circular, square, triangular, rectangular or any other given shape. Additionally the sampling means can be designed in any given shape although the preference is a circular shape. The sampling means could be fitted with a cover if so desired. The spherical element can be made of the same material as the rest of the device or it could be composed of a flexible material such as rubber. The end of the hook could be rounded, pointed, or blunt. The pool maintenance device can be manufactured in a variety of sizes and colors. There are, of course, additional features of the invention that will be described hereinafter and which will form the subject matter of the claims attached.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved pool maintenance device that has all of the advantages of the prior art fluid collection devices and none of the disadvantages.

It is another object of the present invention to provide a new and improved pool maintenance device that may be easily and efficiently manufactured and marketed.

An even further object of the present invention is to provide a new and improved pool maintenance device that has a low cost of manufacture with regard to both materials and labor, and which accordingly is then susceptible of low prices of sale to the consuming public, thereby making such pool maintenance device economically available to the buying public.

Still another object of the present invention is to provide a new pool maintenance device that provides in the apparatuses and methods of the prior art some of the advantages thereof, while simultaneously overcoming some of the disadvantages normally associated therewith.

Even still another object of the present invention is to provide a pool maintenance device that eliminates the use of several tools for pool maintenance. The present device allows all pool maintenance to be accomplished with the use of one tool. People will no longer have to worry about misplacing a tool or having to search for different tools to perform various pool tasks. Even pool chemical testing kits can be stored within the sampling container of the tool for easy access. This tool also eliminates the strain placed on the body from performing the required maintenance on a pool. There is no need for bending or kneeling on the hard ground near the side of the pool in order to maintain the pool. A person could stand upright to collect a water sample from the pool, remove skimmer covers for cleaning, move a dividing rope line or thermometer, and add chemicals to the pool to achieve a chemical balance. Standing upright to perform these tasks would help eliminate the pain caused by bending or kneeling on the hard ground for those with knee, back, or hip problems. Another advantage is that one would no longer have to get any part of his/her body wet in order to check the chemical composition of the pool water or to check the temperature of the pool water.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various figures.

DRAWINGS-REFERENCE NUMERALS

Figure 1:
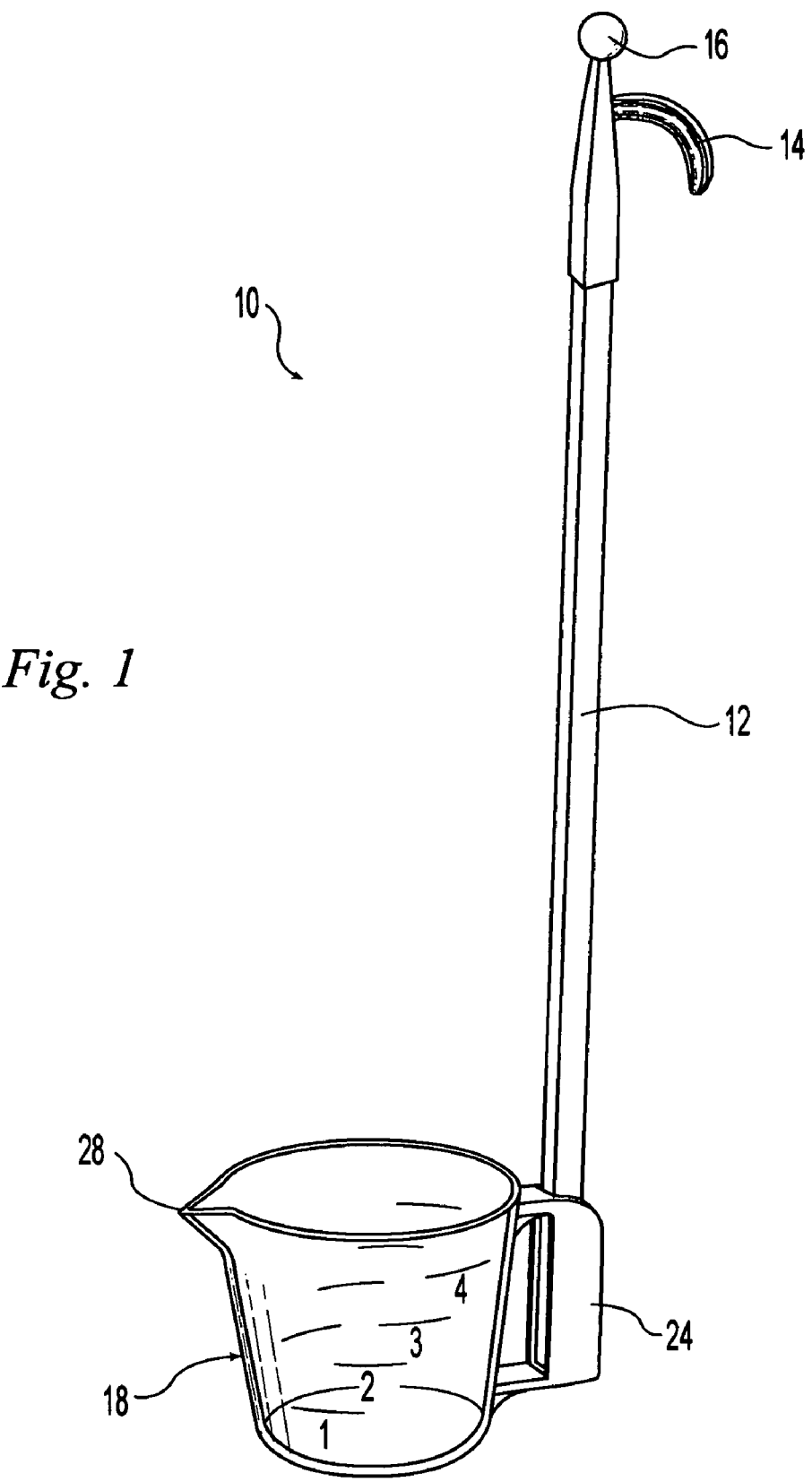
FIG. 1 is a perspective view of the preferred embodiment of the pool maintenance device constructed in accordance with the principles of the present invention.

10 pool maintenance device
12 rod
14 hook
16 spherical element
18 sampling container
20 outer wall
22 bottom member
24 handle means
26 graduations
28 discharge facilitation area
30 hook assembly
32 base of hook assembly
34 female receptacle of hook assembly
36 female receptacle of sampling container

DESCRIPTION OF THE PREFERRED EMBODIMENT

Figure 2:
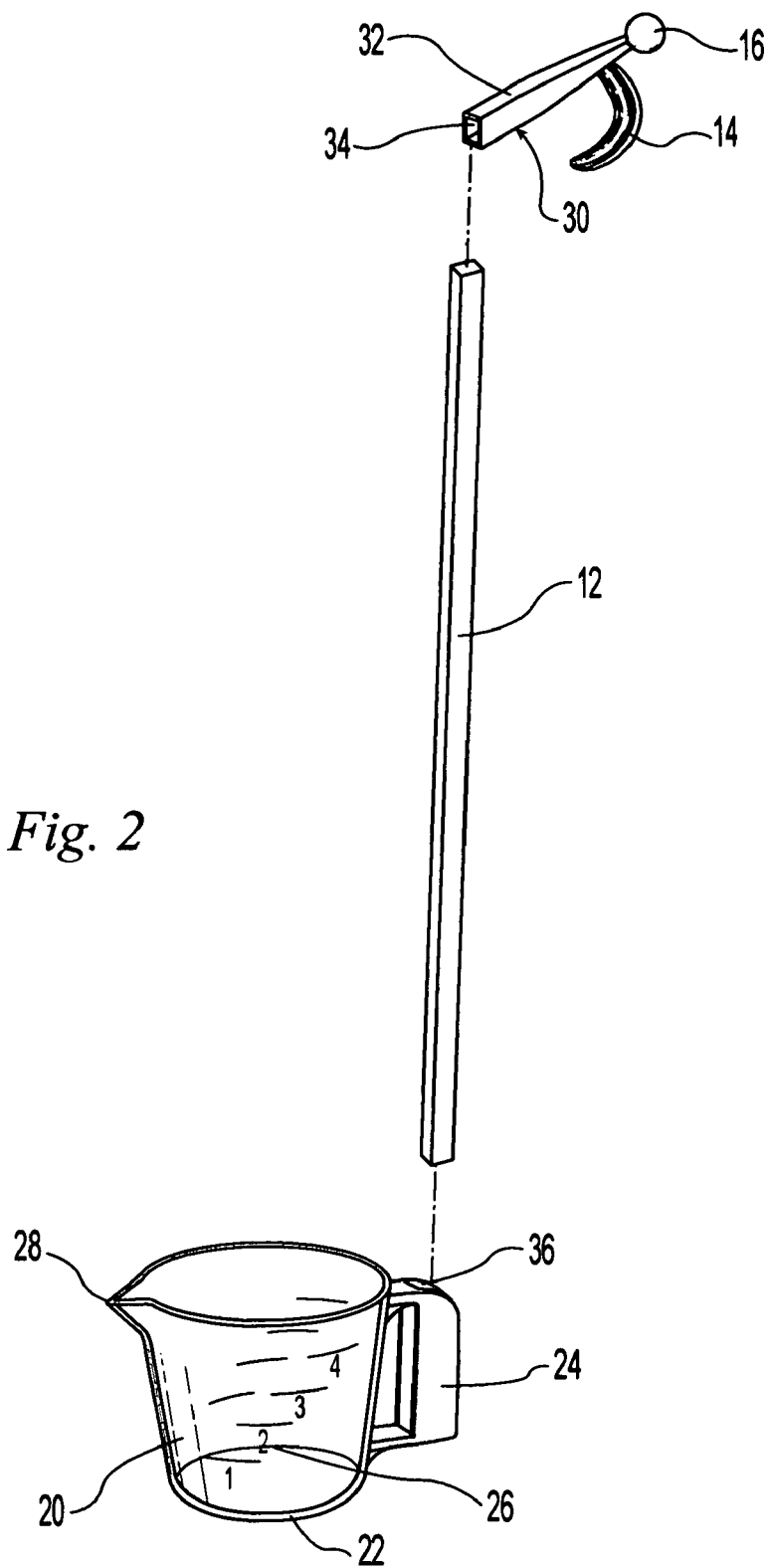
FIG. 2 is an exploded perspective view of the pool maintenance device of the present invention showing the interconnection of the rod to the hook assembly and the sampling container.

Referring now to the drawings, and particularly to FIGS. 1–3, a preferred embodiment of the pool maintenance device of the present invention is shown and generally designated by the reference numeral 10.

In FIG. 1, a new and improved pool maintenance device 10 of the present invention for providing an all-in-one product for pool maintenance that eliminates any strain on the body is illustrated and will be described. More particularly, the pool maintenance device 10 is comprised of an elongated rigid rod 12 with opposing first and second end sections wherein the first end section is attached to a hook assembly 30 and the second end section is attached to a sampling container 18. The rod 12 can be manufactured in a variety of shapes, however it is preferably formed of a square configuration. The rod 12 can be made to any predetermined length but is preferably at least 40 inches long. The rod 12 can also be made to any desired thickness however a ¾ inch thickness is preferable. The pool maintenance device 10 can be manufactured of a variety of materials such as stainless steel, heavy gauge metal, or a hard impact plastic. A hard impact plastic is the preferred choice of composition.

FIG. 2 shows the interconnection of the rod 12, hook assembly 30, and sampling container 18 to assemble the pool maintenance device 10. A hook assembly 30 consisting of a base 32, a hook 14, and a spherical element 16 is attached to the first end section of the rod 12. The hook assembly 30 is preferably 6 inches in length but can be manufactured in a variety of sizes. The base 32 of the hook assembly 30 can be manufactured in a variety of shapes but is preferably essentially comprised of a four-sided pyramidal first end portion positioned directly atop a hollow cube-shaped second end portion. The second end portion of the base 32 is preferably of the same general configuration as the shape of the rod 12. The second end portion of the base 32 preferably forms a female receptacle 34 into which the first end section of the rod 12 is inserted. When inserted, the first end section of the rod 12 lies integral with the female receptacle 34 of the hook assembly 30. In an alternative embodiment, the first end section of the rod 12 could contain a female receptacle which could receive a male connector that extends from the second end portion of the base 32 of the hook assembly 30. This male connector would be of the same configuration as the female receptacle within the first end section of the rod 12. The spherical element 16 is fixedly attached to the apex of the first end section of the base 32 of the hook assembly 30. The spherical element 16 can be manufactured in a variety of sizes, but preferably is ½ inch in diameter so as to allow it to fit into the hole in the top of a skimmer cover to lift off the skimmer cover for cleaning of the skimmer baskets. The spherical element 16 can be made of the same material as the rest of the pool maintenance device 10 or it could be manufactured using rubber or nylon to allow for stretching and compression when the spherical element 16 is inserted into one of the skimmer cover holes. The spherical element 16 can either be solid or hollow but is preferably solid. The hook 14 preferably extends laterally from the midpoint of the base 32 where the first end portion of the base 32 and the second end portion of the base 32 meet. The hook 14 is positioned essentially perpendicular to the spherical element 16. The hook 14 preferably curves downwardly from the base 32 to be used as a handle when using the pool maintenance device 10 as a fluid sampler. The distance between the end of the hook 14 and the base 32 is preferably 3½ inches. The hook 14 could have a pointed, rounded, or blunt end but the preference is for a rounded end in order to reduce any potential injuries.

The sampling container 18 is comprised of a continuous outer wall 20 having upper and lower portions. A bottom member 22 is integrally attached to the lower portion of the outer wall 20 of the container 18. The upper portion of the container 18 is preferably open. There is a discharge facilitation area 28 extending laterally from the rim of the upper portion of the container 18. It is preferable that the discharge facilitation area 28 have a triangular construction with the tip of the triangle shape extending laterally away from the outer wall 20. A handle means 24 is affixed to the upper portion of the outer wall 20 of the container 18 such that it is diametrically opposed to the discharge facilitation area 28. The handle means 24 will preferably be comprised of two essentially horizontal members each having opposing ends and an essentially vertical member also having opposing ends. One end of each horizontal member is fixedly attached to the outer wall 20 of the container 18 so that the horizontal members are positioned parallel to each other and the distance between the horizontal members is equal to the length of the vertical member of the handle means 24. One end of the vertical member of the handle means 24 is attached to the opposing end of the first horizontal member of the handle means 24. The opposing end of the vertical member of the handle means 24 is attached to the opposing end of the second horizontal member of the handle means 24. The vertical member of the handle means 24 is hollow to form a female receptacle 36 in the handle means 24 of the container 18. The rod 12 extends downward from the hook assembly 30 to have the second end section of the rod 12 act as a male attachment member that can be inserted into the female receptacle 36 in the handle means 24 of the container 18. The second end section of the rod 12 is inserted into the female receptacle 36 of the handle means 24 of the container 18 so that the second end section of the rod 12 lies integral with the inner surface of the female receptacle 36 in the handle means 24 of the container 18. The container 18 is preferably attached to the rod 12 so that it is positioned on the opposite side of the hook 14 of the hook assembly 30. For stability of the handle means 24 support arches can be placed below each horizontal member of the handle means 24. These arches would have opposing ends wherein one end would attach to the outer wall 20 of the container 18 and the opposing end would attach to the vertical member of the handle means 24. The container 18 can be of any predetermined size, but preferably will be capable of holding four cups of chemicals. The container 18 can be manufactured in many different colors, however it is preferable that the container 18 is translucent so as to allow the viewer to be able to see the contents within the container 18. The container 18 will also preferably be made of a hard plastic material, such as a high impact styrene, but could also be manufactured of stainless steel or a heavy gauge metal. Preferably the container 18 will be molded in a single operation by any one of a number of commercially available molding machines. The container 18 will have graduations 26 formed along one wall of the container 18. The graduations 26 are preferably in metric units while the graduations 26 on the diametrically opposed outer wall 20 of the container 18 are in English units. These graduations 26 provide an easy indication of the volume of liquid in the container 18 for mixing chemicals to put in the pool. The graduations 26 are preferably written at an upwards slant with the lowest amount written at the lower left corner of the container 18 and the highest amount written at the upper right corner of the container 18. The graduations 26 may be written in any number of ways such as with raised lettering, engraved lettering, or painted lettering, but the preference is for raised lettering. The graduations 26 can be written in any of a variety of colors, but preferably are written in colors that are easily seen when liquid is in the container 18.

In the alternative, the pool maintenance device 10 can be manufactured as one piece in a single operation by any of a number of commercially available molding machines. In this alternative, neither the female receptacle 34 of the hook assembly 30 nor the female receptacle 36 in the handle means 24 of the container 18 is needed. In this alternative, the rod 12 itself would form the vertical portion of the handle means 24 on the container 18 and would extend upwardly from the container 18 to terminate in a spherical element 16. A downwardly curving hook 14 would extend laterally from the rod 12 directly beneath the spherical element 16. There would be no separate base 32 part that the hook 14 and spherical element 16 would connect to. The hook 14 and the spherical element 16 would each be an extension of the first end section of the rod 12. The container 18 would be an extension of the second end section of the rod 12. All other elements would remain the same.

Figure 3A:
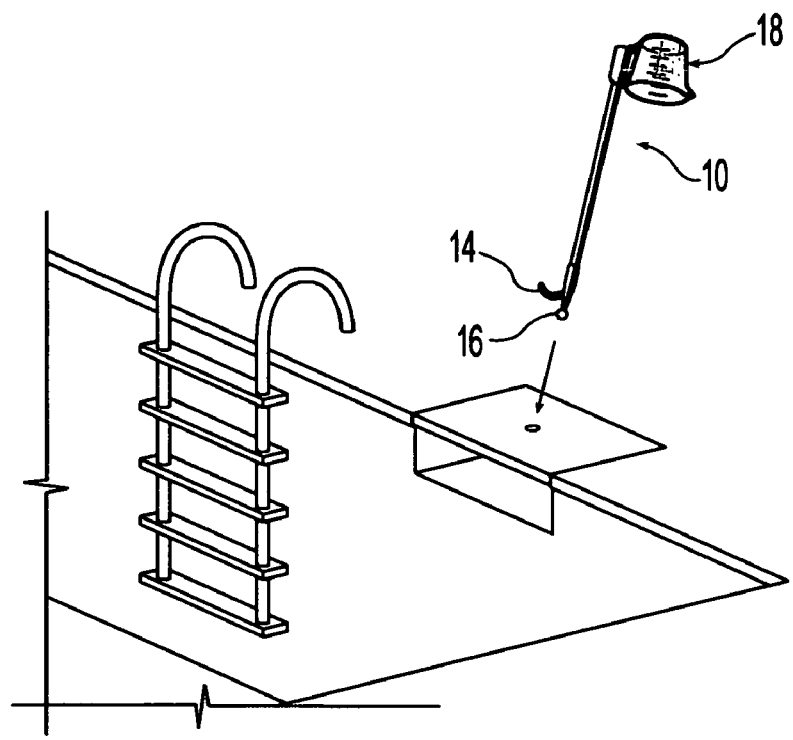
FIG. 3a is a perspective view of the pool maintenance device of the present invention showing the insertion of the spherical element into the skimmer cover.
Figure 3B:
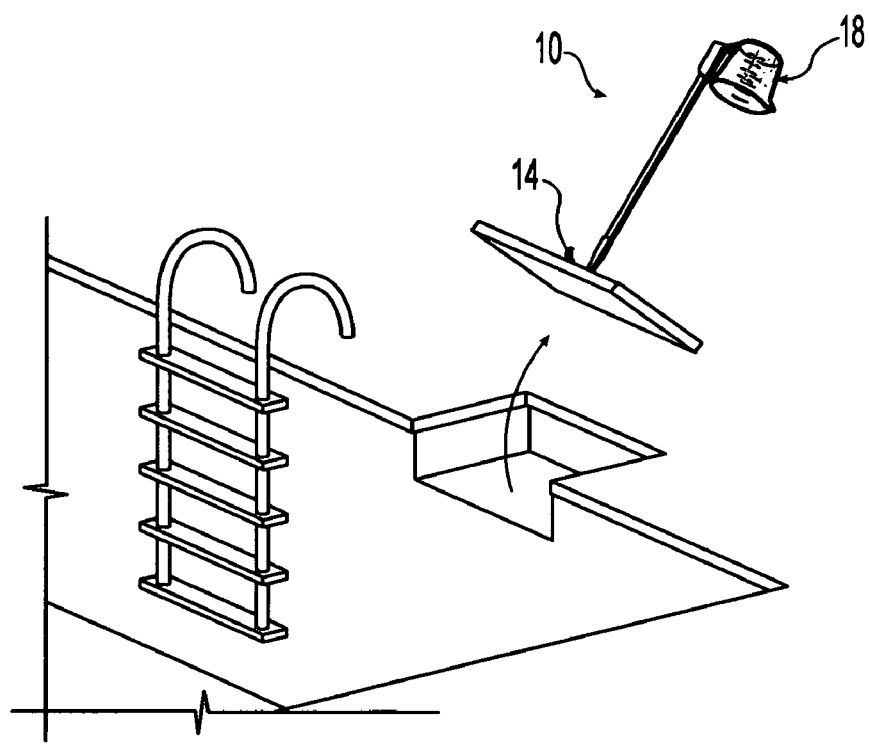
FIG. 3b is a perspective view of the pool maintenance device of the present invention showing the actual removal of the skimmer cover for cleaning.

FIG. 3 shows the pool maintenance device 10 in use to lift the skimmer covers for cleaning of the skimmer baskets. As shown in FIG. 3a, one would grasp the handle means 24 of the container 18 of the pool maintenance device 10 and orient the pool maintenance device 10 so that the spherical element 16 is pointing downward toward the pool deck. One would then insert the spherical element 16 of the pool maintenance device 10 into the hole at the top of the skimmer cover and lift the pool maintenance device 10 so that the skimmer cover is lifted off of the skimmer as shown in FIG. 3*b*. One can use the same technique to remove the skimmer baskets for cleaning.

In use as a fluid sampling device, a person would grip the hook 14 with their hand and lower the pool maintenance device 10 into the swimming pool water so that the container 18 is immersed at least 18 inches below the water's surface. One would then raise the pool maintenance device 10, which now contains a sample of water that was at least 18 inches below the surface, and conduct chemical testing on the water sample. If chemicals need to be added to the pool, one can measure and mix the chemicals within the container 18 of the pool maintenance device 10. Once ready to add the chemicals to the pool water, one simply grips the handle means 24 attached to the sampling container 18 of the pool maintenance device 10 and tips the container 18 over the pool so that the chemicals pour out of the discharge facilitation area 28 and into the pool water.

In use to move the dividing rope line in a pool, one would grasp the handle means 24 of the sampling container 18 of the pool maintenance device 10 so that the spherical element 16 is positioned towards the ground. One would then insert the pool maintenance device 10 into the pool water with the end of the hook 14 facing downwards into the water. One would move the hook 14 until the free end of the hook 14 is positioned beneath the rope dividing line. One would then move the pool maintenance device 10 so that the rope dividing line is placed adjacent to the curve of the hook 14. The rope dividing line can then be manipulated into any alternate position.

In use to check the pool temperature, one would again grasp the handle means 24 of the sampling container 18 of the pool maintenance device 10 and position the pool maintenance device 10 so that the spherical element 16 is facing the ground. The hook 14 is then inserted into the pool water vertically until the attachment string of the pool thermometer is resting adjacent to the curve of the hook 14. The pool maintenance device 10 is then lifted vertically until the pool thermometer can be grasped.

While a preferred embodiment of the pool maintenance device 10 has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A pool maintenance device comprising:
   a rigid elongated rod of a predetermined length having first and second opposing end sections;
   a hook extending laterally from said first end section of said rod;
   a spherical element projecting upwardly from said first end section of said rod;
   a container having a continuous outer wall with said outer wall including an upper portion and a lower portion, a bottom member integral with said lower portion of said outer wall to form a receptacle therein and a handle means wherein said second end section of said rod is fixedly attached to said handle means.

2. The device of claim 1, wherein said hook is positioned essentially opposite said container.

3. The device of claim 1, wherein said spherical element is of a predetermined size.

4. The device of claim 1, wherein said spherical element is positioned essentially perpendicular to said hook.

5. The device of claim 1, wherein said upper portion of said container forms an open top.

6. The device of claim 1, wherein a discharge facilitation area extends laterally from said upper portion of said outer wall of said container.

7. The device of claim 6, wherein said container includes graduations on said outer wall.

8. A pool maintenance device comprising:
   a rigid elongated rod of a predetermined length having first and second opposing end sections;
   a hook assembly comprised of a base having first and second opposing end portions, a downwardly curving hook wherein said hook extends laterally from said base, and a spherical element of a predetermined size projecting upwardly from said first end portion of said base, wherein said hook assembly is fixedly attached to said first end section of said rod;
   a container comprised of a continuous outer wall with said outer wall including an upper portion and a lower portion wherein said upper portion is open, a bottom member integral with said lower portion of said outer wall to form a receptacle therein, and a handle means wherein said handle means is fixedly attached to said second end section of said rod.

9. The device of claim 8, wherein said second end portion of said base of said hook assembly is essentially of the same configuration as said first end section of said rod.

10. The device of claim 8, wherein said hook is positioned essentially opposite said container.

11. The device of claim 8, wherein said spherical element is positioned essentially perpendicular to said hook.

12. The device of claim 8, wherein a discharge facilitation area extends laterally from said upper portion of said outer wall of said container.

13. The device of claim 12, wherein said container has graduations on said outer wall.

14. A pool maintenance device comprising:
   a rigid elongated rod of a predetermined length said rod having opposing first and second end sections;
   a hook assembly comprised of a base having first and second opposing end portions, a downwardly curving hook wherein said hook extends laterally from said base, and a spherical element of a predetermined size projecting upwardly from said first end portion of said base so that said spherical element is positioned essentially perpendicular to said hook, wherein said hook assembly is fixedly attached to said first end section of said rod;
   a container comprised of a continuous outer wall with said outer wall including an upper portion and a lower portion wherein said upper portion is open, a bottom member integral with said lower portion of said outer wall to form a receptacle therein, a discharge facilitation area extending laterally from said upper portion of said outer wall of said container, and a handle means wherein said handle means is fixedly attached to said second end section of said rod.

15. The device of claim 14, wherein said second end portion of said base of said hook assembly includes a female receptacle therein.

16. The device of claim 15, wherein said first end section of said rod is inserted into said female receptacle of said base of said hook assembly to lie integral with said female receptacle of said base of said hook assembly.

17. The device of claim 14, wherein said hook is positioned essentially opposite said container.

18. The device of claim 14, wherein said handle means includes a female receptacle.

19. The device of claim 18, wherein said second end section of said rod is inserted into said female receptacle of said handle means to lie integral with said female receptacle of said handle means.

20. The device of claim 14, wherein said container has graduations on said outer wall.

* * * * *